(12) United States Patent
Esposito et al.

(10) Patent No.: US 7,270,806 B2
(45) Date of Patent: *Sep. 18, 2007

(54) LIQUID STICK ANTIPERSPIRANT

(75) Inventors: Anthony Esposito, Roselle, NJ (US);
Thomas Schamper, Cranbury, NJ (US);
Eddie Carl Henry, Flanders, NJ (US)

(73) Assignee: Coty S.A., Paris (FR)

( * ) Notice: Subject to any disclaimer, the term of this patent is extended or adjusted under 35 U.S.C. 154(b) by 142 days.

This patent is subject to a terminal disclaimer.

(21) Appl. No.: 10/710,646

(22) Filed: Jul. 27, 2004

(65) Prior Publication Data

US 2006/0024252 A1 Feb. 2, 2006

(51) Int. Cl.
*A61Q 15/00* (2006.01)
*A61K 8/00* (2006.01)
*A61K 8/02* (2006.01)

(52) U.S. Cl. .................. 424/65; 424/66; 424/68; 424/400; 424/401

(58) Field of Classification Search .................. 424/65, 424/66, 68, 400, 401
See application file for complete search history.

(56) References Cited

U.S. PATENT DOCUMENTS

| | | | | |
|---|---|---|---|---|
| 5,643,558 A | * | 7/1997 | Provancal et al. | ............ 424/66 |
| 5,871,720 A | * | 2/1999 | Gutierrez et al. | ............. 424/65 |
| 6,180,125 B1 | | 1/2001 | Ortiz et al. | |
| 6,338,841 B1 | * | 1/2002 | Mattai et al. | ................. 424/65 |
| 2002/0048557 A1 | | 4/2002 | Cai et al. | |
| 2006/0073108 A1 | | 4/2006 | Esposito et al. | |

FOREIGN PATENT DOCUMENTS

WO    WO-2006014962 A3    2/2006

OTHER PUBLICATIONS

"International Search Report and Written Opinion for Application No. PCT/US05/26502, date mailed Jul. 27, 2005", 8 Pages.

* cited by examiner

*Primary Examiner*—Shelley A. Dodson
(74) *Attorney, Agent, or Firm*—Schwegman, Lundberg & Woessner P.A.

(57) ABSTRACT

One embodiment of the invention described herein includes a method for improving stability of an antiperspirant. The method includes preparing a blend that comprises propylene glycol and dibenzylidene sorbitol; adding an antiperspirant active solid powder to the blend, to make an antiperspirant blend, in a concentration effective for making an antiperspirant that provides antiperspirant protection to a user and improves process stability of the antiperspirant; and adding an amino acid salt to the antiperspirant blend in a concentration effective for stabilizing the dibenzylidene sorbitol.

23 Claims, No Drawings

LIQUID STICK ANTIPERSPIRANT

TECHNICAL FIELD

The present invention relates to a liquid stick antiperspirant, and to a method for making the liquid stick antiperspirant.

BACKGROUND ART

Antiperspirants have as a principle function, a requirement to eliminate adverse effects of perspiration. Antiperspirant function has frequently been associated with undesirable side effects. One undesirable side effect has been stickiness. Dimethicone and other silicones have been added to reduce tack in antiperspirants, as described in U.S. Pat. No. 6,180,125 and U.S. Patent Appln. Publ. No. 20020048557. Solutions to stickiness have, however, produced problems of instability in the antiperspirant formulations.

DISCLOSURE OF INVENTION

One embodiment of the invention described herein includes a method for improving process stability and self stability of an antiperspirant product. The method includes preparing a blend that comprises propylene glycol, dibenzylidene sorbitol, and adding an antiperspirant active material to the blend in a concentration effective for making an antiperspirant that provides antiperspirant protection to a user while improving process stability of the antiperspirant. The method also includes adding a salt of an amino acid, wherein the salt is effective for buffering the degradative acid hydrolysis of the dibenzylidene sorbitol (DBS).

Another embodiment of the invention described herein includes an antiperspirant wherein the structurant, carrier, and antiperspirant consist essentially of propylene glycol, dibenzylidene sorbitol, and solid active antiperspirant. The antiperspirant additionally includes a salt of an amino acid effective for buffering the degradative acid hydrolysis of the dibenzylidene sorbitol.

One other embodiment of the invention includes an antiperspirant consisting essentially of propylene glycol, dibenzylidene sorbitol, solid active antiperspirant, a salt of an amino acid effective for buffering the degradative acid hydrolysis of the dibenzylidene sorbitol, and hydroxylpropyl cellulose.

Another embodiment of the invention includes an antiperspirant consisting essentially of propylene glycol, dibenzylidene sorbitol, solid active antiperspirant, a salt of an amino acid effective for buffering the degradative acid hydrolysis of the dibenzylidene sorbitol, and stearyl alcohol.

One other embodiment includes an antiperspirant comprising a structurant, carrier, fragrance and antiperspirant, wherein the structurant, carrier, fragrance and antiperspirant consist essentially of propylene glycol, dibenzylidene sorbitol, solid active antiperspirant, and fragrance. The antiperspirant also includes a salt of an amino acid effective for buffering the degradative acid hydrolysis of the dibenzylidene sorbitol.

Another embodiment includes an antiperspirant consisting essentially of propylene glycol, dibenzylidene sorbitol, solid active antiperspirant, hydroxypropyl cellulose, a salt of an amino acid effective for buffering the degradative acid hydrolysis of the dibenzylidene sorbitol, and stearyl alcohol.

One additional embodiment of the invention described herein includes a method for improving process stability of an antiperspirant comprising employing dibenzylidene sorbitol and a solid active antiperspirant to make the antiperspirant and adding a salt of an amino acid effective for buffering the degradative acid hydrolysis of the dibenzylidene sorbitol.

One embodiment of the invention described herein relates to an antiperspirant that includes a propylene glycol carrier in a concentration of 65 to 90 percent by weight; hydroxypropyl cellulose in a concentration of zero to 1.0 percent by weight; a structurant that includes dibenzylidene sorbitol in a concentration of 0.5 to 3.0 percent by weight; an antiperspirant active that includes solids in a concentration of 5 to 25 percent by weight and fragrance in a concentration of zero to 3 percent by weight. The formulation also includes a salt of an amino acid effective for buffering the degradative acid hydrolysis of the dibenzylidene sorbitol. The formulation embodiments of the invention described herein produce an antiperspirant having low tack and process stability.

The stability and low tack features of the antiperspirant of the invention described herein are surprising because formulations containing dibenzylidene sorbitol (DBS) have heretofore been characterized as being sticky and susceptible to degradation of the dibenzylidene sorbitol. These prior art formulations have typically included emollients, dimethicone or other type of silicone in order to reduce tackiness.

Embodiments of the invention described herein remedies the problems of low tack and instability by preparing a formulation wherein solid, suspended antiperspirant active ingredients are added to a formulation containing DBS, instead of a solution of said antiperspirant salts. Additionally, the method of the invention includes adding a salt of an amino acid, which is effective for buffering the degradative acid hydrolysis of the dibenzylidene sorbitol.

The solid particulate antiperspirant amino acid salt slows the degradation of the dibenzylidene sorbitol, as compared to degradation of DBS by soluble antiperspirant actives employed in prior art clear antiperspirant sticks. The formulation embodiments described herein do not require the presence of dimethicone or other silicone type to reduce tackiness.

The antiperspirant of the invention described herein is low tack and stable because the use of solid antiperspirant active material such as aluminum zirconium tetrachlorhydrex glycine complex, along with zinc glycinate solid powder buffers the acidity of the antiperspirant salt. Combination with the dibenzylidene sorbitol structurant having a concentration of about 0.5 to 3.0% by weight creates an antiperspirant suspension that degrades much more slowly than soluble active antiperspirants. The propylene glycol concentration of 65 to 90% by weight disperses and dissolves the structurant at elevated temperatures to formulate an antiperspirant product having improved stability over conventional antiperspirants containing dibenzylidene sorbitol.

The term "structurant" as used herein refers to an additive used to suspend particles, and to thicken a suspension or to form solid gels. Dibenzylidene sorbitol, hydroxypropylcellulose and stearyl alcohol are structurants.

Solid active antiperspirants suitable for use in the invention described herein include aluminum zirconium tetrachlorhydrex glycine complex with zinc glycinate and aluminum zirconium tetrachlorhydrex glycine complex with a salt other than zinc glycinate such as sodium glycinate and other water soluble amino acid salts such as sodium arginate. Other active solid antiperspirants include aluminum chlorhydrate, aluminum sesquichhlorhydrate, aluminum zirconium trichlorohydrate glycine, aluminum zirconium pentachlorohydrex glycine, aluminum zirconium tetrachlorohydrex glycine and aluminum zirconium octochlorohydrex glycine. The aluminum zirconium-containing materials are commonly referred to as antiperspirant active aluminum zirconium salts. Generally, the foregoing metal antiperspirant active materials are antiperspirant active metal salts listed in the Federal Register, Vol. 68, No. 110/Monday, Jun. 9, 2003/Rules and Regulations.

Fragrances suitable for use in the invention described herein include natural products such as essential oils, flower oils, natural extracts from resins, gums, balsams, beans, mosses and other plants, and animal products such as ambergris and musk, as well as synthetic aromatic materials. It is believed that any fragrance material is suitable for use in the invention described herein. Suffice it to say that the fragrance materials generally fall into several well known categories, such as floral, spicy, woody, mossy, oriental, herbal, leather-tobacco and aldehydic groups. Men's fragrances suitable for use in the invention are classified into citrus, spice, leather, lavender, woody groups. Typically, fragrance materials are supplied as concentrates which generally contain up to about 3 percent fragrance by weight. Fragrance is optional and formulation embodiments of the invention described herein are not required to include a fragrance.

The hydroxypropyl cellulose is added as a structurant. Hydroxypropyl cellulose, when present in antiperspirant formulation embodiments, is present in concentrations of up to 1.0%. One problem with using DBS as the only structurant in a gelled stick is that the resulting product displays excessive syneresis, the weeping of liquid from the gelled solid. This syneresis is due to a low viscosity of the continuous liquid phase of the gel. The liquid seeps from the solid because of the capillary action. The hydroxyl propyl cellulose increases the viscosity of the liquid phase and dramatically decreases the syneresis.

Stabilizers suitable for use in some formulation embodiments of the invention include particulate organic or inorganic materials which are dispersible or dissolvable in the formulation. Other stabilizers usable for some formulations in the invention described herein include silica, mineral pigments, organic pigments, crosslinked polymers and copolymers of acrylic acid, cellulose ethers and mixtures thereof. Other stabilizers suitable for use include silica and mineral pigments. Examples of mineral pigments include, but are not limited to calcium carbonate, titanium dioxide, clay, organophilic clay, talc and gypsum. Cellulose ethers suitable for use as stabilizers include carboxymethyl cellulose and hydroxypropyl cellulose.

One formulation embodiment also includes stearyl alcohol as a structural component. Formulations that include stearyl alcohol have stearyl alcohol concentrations up to about 15% by weight. Other materials suitable for use in the invention, that impart structure include organic structurants that are non-polymeric or polymeric. Non-polymeric structurants, including waxes and gellants, are often selected from fatty acids or salts thereof, often containing from 12 to 30 carbons such as stearic acid or sodium stearate, and/or fatty alcohols (typically insoluble in water) often containing from 12 to 30 carbons. The term "fatty" as used herein refers to a long chain aliphatic group, such as at least 8 or 12 linear carbons, which is frequently not branched (linear) and is typically saturated, but which can alternatively be branched and/or unsaturated. It is possible for the fatty acid to contain an hydroxyl group, as in 12-hydroxystearic acid, for example as part of a gellant combination, and to employ amido or ester derivatives thereof. Examples of suitable higher molecular weight alcohols include behenyl alcohol and sterols such as lanosterol.

The dibenzylidene sorbitol also functions as a structurant and acts in combination with other structurants in the formulation, such as stearyl alcohol, for some embodiments. These structurants are believed to operate by interactions which are permanent unless disrupted by shear or heating. These structurants form a network of strands or fibers extending throughout a gelled liquid antiperspirant. In some cases, the fibers are observable by electron microscopy, although in other cases the observation of the fibers which are believed to be present is prevented by practical difficulties in preparing a suitable specimen. When observed, the primary fibers in a gel are generally thin (diameter less than 0.5μ, often less than 0.2μ) and appear to have numerous branches or interconnections. Primary fibers may entwine to form a thicker strand.

For some embodiments, fibers are crystalline. If the fibers are crystalline, they may or may not be the same polymorph as macroscopic crystals obtained by conventional crystallization from a solvent.

One liquid carrier material used in the present invention is propylene glycol. Other suitable liquid carriers include organic solvents. Suitable organic solvents have a melting point of less than 10° C., such as less than 5° C. This melting point range benefits both low temperature storage stability and ease of manufacture. A class of organic solvents suitable for use in the invention described herein are aliphatic alcohols (monohydric or polyhydric, preferably having 2 to 8 carbon atoms) and polyglycol ethers, preferably oligoglycol ethers having only 2 to 5 repeat units. Examples include dipropylene glycol, glycerol propylene glycol, butylene glycol, ethanol, propanol, isopropanol, and industrial methylated spirits. Suitable organic solvents include aliphatic alcohols, in particular those having 2 to 3 carbon atoms, especially ethanol and isopropanol.

Mixtures of carrier materials are also usable. The total amount of carrier material employed is for some embodiments, from 30% to 99%, and for other embodiments, from 60% to 98%, expressed as a weight percentage of the total weight of the composition.

The formulation of the invention described herein is made, for one embodiment, by adding hydroxypropyl cellulose to propylene glycol and blending to make a solution. The dibenzylidene sorbitol is added to the solution to gel the solution and to act as a structurant, forming a network of fibers within the solution. Stearyl alcohol is added for some embodiments and also acts as a structurant. The aluminum zirconium tetrachlorhydrex glycine complex with zinc glycinate is then added to make a final antiperspirant product mixture.

The final antiperspirant product mixture is added to a packaging that is capable of shaping and holding a stick. In one embodiment, the packaging is polymeric. The antiperspirant mixture takes the shape of the container. The container is labeled with indicia branding the antiperspirant mixture and providing other information such as, for example, ingredients.

Although the invention has been described with reference to specific forms thereof, it will be understood that many changes and modifications may be made without departing from the spirit of this invention.

The invention claimed is:

1. A method for improving stability of an antiperspirant, comprising:

preparing a blend that comprises propylene glycol and dibenzylidene sorbitol; adding an antiperspirant active solid powder to the blend, to make an antiperspirant blend, in a concentration effective for making an antiperspirant that provides antiperspirant protection to a user and improves process stability of the antiperspirant; and adding an amino acid salt to the antiperspirant blend in a concentration effective for stabilizing the dibenzylidene sorbitol.

2. The method of claim 1 wherein the amino acid salt stabilizes the dibenzylidene sorbitol for process temperatures up to 105° C.

3. The method of claim 1 further comprising adding the antiperspirant to a container.

4. The method of claim 3 further comprising labeling the container with indicia containing instructions for using the antiperspirant.

5. The method of claim 1 further comprising adding hydroxypropyl cellulose to the blend.

6. The method of claim 1 further comprising adding stearyl alcohol to the blend.

7. The method of claim 1 further comprising adding fragrance to the antiperspirant.

8. The method of claim 1 wherein the aluminum zirconium tetrachlorhydrex glycine complex added further includes zinc glycinate.

9. A product made by the process of claim 1.

10. An antiperspirant wherein the structurant, carrier, antiperspirant and antiperspirant stabilizer consist essentially of propylene glycol, dibenzylidene sorbitol, solid active antiperspirant, and an amino acid salt in a concentration effective for stabilizing the dibenzylidene sorbitol.

11. The antiperspirant of claim 9 wherein the propylene glycol concentration is within a range of about 65 to 90% w/w.

12. The antiperspirant of claim 9 wherein the dibenzylidene sorbitol concentration is within a range of about 0.5 to 3.0% w/w.

13. The antiperspirant of claim 9 wherein the solid active antiperspirant comprises aluminum zirconium tetrachlorohydrex glycine complex.

14. The antiperspirant of claim 12 wherein the aluminum zirconium tetrachlorohydrex glycine complex further comprises zinc glycinate.

15. An antiperspirant consisting essentially of propylene glycol, dibenzylidene sorbitol, solid active antiperspirant, and hydroxypropyl cellulose.

16. An antiperspirant consisting essentially of propylene glycol, dibenzylidene sorbitol, solid active antiperspirant, hydroxypropyl cellulose, stearyl alcohol, and an amino acid salt in a concentration effective for stabilizing the dibenzylidene sorbitol.

17. The antiperspirant of claim 13 further comprising fragrance.

18. A method for improving process stability of an antiperspirant comprising employing dibenzylidene sorbitol and a solid active antiperspirant to make the antiperspirant, and adding an amino acid salt to the antiperspirant in a concentration effective for stabilizing the dibenzylidene sorbitol.

19. An antiperspirant formulation comprising dibenzylidene sorbitol, an antiperspirant having a solid powder form and an amino acid salt effective for stabilizing the dibenzylidene sorbitol.

20. The antiperspirant formulation of claim 19 wherein the amino acid salt is zinc glycinate.

21. The antiperspirant formulation of claim 19 wherein the amino acid salt is sodium arginate.

22. The antiperspirant formulation of claim 19 wherein the amino acid salt is sodium glycinate.

23. An antiperspirant formulation comprising dibenzylidene sorbitol, an antiperspirant having a solid powder form and an amino acid salt effective for stabilizing the dibenzylidene sorbitol, the antispirant formulation being substantially free of dimethicone.

* * * * *

UNITED STATES PATENT AND TRADEMARK OFFICE
CERTIFICATE OF CORRECTION

PATENT NO. : 7,270,806 B2 Page 1 of 1
APPLICATION NO. : 10/710646
DATED : September 18, 2007
INVENTOR(S) : Esposito et al.

It is certified that error appears in the above-identified patent and that said Letters Patent is hereby corrected as shown below:

In column 5, line 25, in Claim 8, delete "tetrachlorhydrex" and insert -- tetrachlorohydrex --, therefor.

In column 6, line 35, in Claim 23, delete "antispirant" and insert -- antiperspirant --, therefor.

Signed and Sealed this

First Day of January, 2008

JON W. DUDAS
*Director of the United States Patent and Trademark Office*